(12) United States Patent
Lamberty et al.

(10) Patent No.: US 9,415,002 B2
(45) Date of Patent: *Aug. 16, 2016

(54) POLYSILICONE BASE FOR SCAR TREATMENT

(71) Applicant: ENGLEWOOD LAB, LLC, Englewood, NJ (US)

(72) Inventors: Julio Lamberty, Hawthorne, NJ (US); Yi-Chun Lin, Hackensack, NJ (US)

(73) Assignee: Englewood Lab, LLC, Englewood, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,687

(22) Filed: Dec. 22, 2015

(65) Prior Publication Data

US 2016/0106659 A1    Apr. 21, 2016

Related U.S. Application Data

(63) Continuation of application No. 14/564,369, filed on Dec. 9, 2014, now Pat. No. 9,226,890.

(60) Provisional application No. 62/028,915, filed on Jul. 25, 2014, provisional application No. 61/914,168, filed on Dec. 10, 2013.

(51) Int. Cl.
| | | |
|---|---|---|
| *A61K 8/891* | (2006.01) | |
| *A61K 8/25* | (2006.01) | |
| *A61Q 19/00* | (2006.01) | |
| *A61K 8/58* | (2006.01) | |
| *A61K 8/893* | (2006.01) | |
| *A61K 8/02* | (2006.01) | |
| *A61K 47/34* | (2006.01) | |
| *A61L 26/00* | (2006.01) | |
| *A61K 47/02* | (2006.01) | |
| *A61K 47/24* | (2006.01) | |

(52) U.S. Cl.
CPC ............... *A61K 8/891* (2013.01); *A61K 8/0241* (2013.01); *A61K 8/25* (2013.01); *A61K 8/585* (2013.01); *A61K 8/893* (2013.01); *A61K 47/02* (2013.01); *A61K 47/24* (2013.01); *A61K 47/34* (2013.01); *A61L 26/0052* (2013.01); *A61L 26/0066* (2013.01); *A61Q 19/00* (2013.01); *A61K 2800/413* (2013.01); *A61K 2800/594* (2013.01); *A61K 2800/5922* (2013.01); *A61L 2300/412* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 4,865,920 A | 9/1989 | Sweet | |
| 4,954,344 A | 9/1990 | Gale | |
| 5,162,410 A | 11/1992 | Sweet | |
| 5,292,530 A | 3/1994 | McCrea et al. | |
| 5,389,092 A | 2/1995 | Guillemet et al. | |
| 5,413,792 A | 5/1995 | Ninomiya et al. | |
| 5,556,699 A | 9/1996 | Niira et al. | |
| 5,674,285 A | 10/1997 | Quaid | |
| 5,741,509 A | 4/1998 | Kushner | |
| 5,759,560 A | 6/1998 | Dillon | |
| 5,804,168 A | 9/1998 | Murad | |
| 5,833,998 A | 11/1998 | Biedermann et al. | |
| 5,861,149 A | 1/1999 | Ritter | |
| 5,919,476 A | 7/1999 | Fischer et al. | |
| 5,972,320 A | 10/1999 | Moloney et al. | |
| 5,980,923 A | 11/1999 | Dillon | |
| 6,086,863 A | 7/2000 | Ritter et al. | |
| 6,155,265 A | 12/2000 | Hammerslag | |
| 6,183,593 B1 | 2/2001 | Narang et al. | |
| 6,183,766 B1 | 2/2001 | Sine et al. | |
| 6,319,942 B1 | 11/2001 | Perricone | |
| 6,337,076 B1 | 1/2002 | Studin | |
| 6,379,716 B2 | 4/2002 | Santhanam et al. | |
| 6,488,944 B2 | 12/2002 | Narang | |
| 6,503,488 B1 | 1/2003 | Rosen et al. | |
| 6,572,878 B1 | 6/2003 | Blaine | |
| 6,589,541 B2 | 7/2003 | Halston et al. | |
| 6,827,929 B1 | 12/2004 | Lord et al. | |
| 6,911,571 B2 | 6/2005 | Utsugi | |
| 6,932,963 B2 | 8/2005 | Perricone | |
| 7,081,135 B2 | 7/2006 | Smith et al. | |
| 7,101,349 B2 | 9/2006 | Binder et al. | |
| 7,189,384 B2 | 3/2007 | Halston et al. | |
| 7,223,777 B2 | 5/2007 | Sankaranarayanan | |
| 7,241,451 B1 | 7/2007 | Edell et al. | |
| 7,521,434 B2 | 4/2009 | Leshchiner et al. | |
| 7,540,850 B2 | 6/2009 | Guillot | |
| 7,582,609 B2 | 9/2009 | Borras Cuesta et al. | |
| 7,683,234 B2 | 3/2010 | Gurtner et al. | |
| 7,731,983 B2 | 6/2010 | Studin | |
| 7,811,599 B2 | 10/2010 | Lukacs et al. | |
| 7,833,542 B2 | 11/2010 | Studin | |
| 7,934,507 B2 | 5/2011 | Brooks | |
| 7,935,364 B2 | 5/2011 | Masters et al. | |
| 7,939,570 B2 | 5/2011 | Raul et al. | |
| 8,021,683 B2 | 9/2011 | Berlat | |
| 8,071,139 B2 | 12/2011 | Widgerow | |
| 8,084,051 B1 | 12/2011 | Dillon | |
| 8,110,207 B2 | 2/2012 | Cebrian Puche et al. | |
| 8,134,041 B2 | 3/2012 | Etchells | |
| 8,168,850 B2 | 5/2012 | Gurtner et al. | |
| 8,178,115 B2 | 5/2012 | Studin | |
| 8,263,114 B2 | 9/2012 | Berlat | |
| 8,287,475 B2 | 10/2012 | Smithers et al. | |
| 8,303,973 B2 | 11/2012 | Daniloff et al. | |
| 8,324,346 B2 | 12/2012 | Cowsar | |
| 8,399,002 B2 | 3/2013 | Chrysopoulo et al. | |

(Continued)

*Primary Examiner* — Robert S Loewe

(74) *Attorney, Agent, or Firm* — Greenberg Traurig, LLP

(57) ABSTRACT

A polysilicone base for medical and cosmetic compositions includes a dimethicone fluid, a volatile cyclosiloxane, a silicone elastomer, and nanoparticulate silica. The polysilicone base may also include one or more therapeutic agents for reducing the formation and appearance of scar tissue at the site of a wound. The polysilicone base is spreadable, but does not run off of the wound site. The polysilicone base is phase-stable, in that it does not separate into phases.

7 Claims, No Drawings

(56) References Cited

U.S. PATENT DOCUMENTS

| | | | |
|---|---|---|---|
| 8,486,374 B2 | 7/2013 | Tamarkin et al. | |
| 8,517,794 B2 | 8/2013 | Thompson | |
| 8,557,287 B2 | 10/2013 | Schleuning | |
| 8,563,536 B2 | 10/2013 | Armer et al. | |
| 8,563,604 B2 | 10/2013 | Palefsky et al. | |
| 8,580,362 B2 | 11/2013 | Van Den Eede et al. | |
| 8,580,810 B2 | 11/2013 | Kronholm et al. | |
| 8,591,924 B2 | 11/2013 | Zheng | |
| 8,591,940 B2 | 11/2013 | Matloub et al. | |
| 8,591,961 B2 | 11/2013 | Widgerow | |
| 8,592,640 B2 | 11/2013 | Zepeda et al. | |
| 8,597,696 B2 | 12/2013 | Debetencourt | |
| 8,603,505 B2 | 12/2013 | Brown et al. | |
| 8,680,054 B2 | 3/2014 | Haug | |
| 8,707,962 B2 | 4/2014 | Dominguez et al. | |
| 8,734,824 B2 | 5/2014 | Bennett et al. | |
| 8,802,133 B2 | 8/2014 | Guilbaud | |
| 8,859,618 B2 * | 10/2014 | Palefsky | A61L 15/225 424/78.06 |
| 8,871,184 B2 | 10/2014 | Tamarkin et al. | |
| 8,871,267 B2 | 10/2014 | Masters | |
| 8,883,183 B2 | 11/2014 | Sullivan et al. | |
| 8,883,185 B2 | 11/2014 | Bennett et al. | |
| 8,883,190 B2 | 11/2014 | Hodges | |
| 9,226,890 B1 * | 1/2016 | Lamberty | A61K 8/891 |
| 2003/0045554 A1 | 3/2003 | Sankaranarayanan | |
| 2004/0039323 A1 | 2/2004 | Utsugi | |
| 2004/0204391 A1 * | 10/2004 | Studin | A61K 9/7015 514/171 |
| 2005/0100568 A1 * | 5/2005 | De Mul | A61K 8/25 424/401 |
| 2006/0110415 A1 | 5/2006 | Gupta | |
| 2008/0133027 A1 | 6/2008 | Hodges | |
| 2008/0220068 A1 | 9/2008 | Masini-Eteve et al. | |
| 2008/0292560 A1 | 11/2008 | Tamarkin et al. | |
| 2008/0299220 A1 | 12/2008 | Tamarkin et al. | |
| 2009/0028914 A1 | 1/2009 | Sullivan et al. | |
| 2009/0131845 A1 | 5/2009 | Gurtner et al. | |
| 2009/0143333 A1 | 6/2009 | Palefsky et al. | |
| 2009/0155586 A1 | 6/2009 | Maitra et al. | |
| 2009/0226506 A1 | 9/2009 | Masters et al. | |
| 2009/0234382 A1 | 9/2009 | Dillon | |
| 2010/0003236 A1 | 1/2010 | Dalko et al. | |
| 2010/0062085 A1 | 3/2010 | Widgerow | |
| 2010/0111846 A1 | 5/2010 | Boyden et al. | |
| 2010/0113615 A1 | 5/2010 | Boyden et al. | |
| 2010/0124539 A1 | 5/2010 | Hanson | |
| 2010/0196454 A1 | 8/2010 | Keller | |
| 2010/0196478 A1 | 8/2010 | Masters | |
| 2010/0247689 A1 | 9/2010 | Paspaleeva-Kuhn et al. | |
| 2010/0249244 A1 | 9/2010 | Fuller | |
| 2010/0266649 A1 | 10/2010 | Maitra et al. | |
| 2011/0009374 A1 | 1/2011 | Keller | |
| 2011/0033508 A1 | 2/2011 | Vogel et al. | |
| 2011/0105996 A1 | 5/2011 | Mustoe et al. | |
| 2011/0123547 A1 | 5/2011 | Armer et al. | |
| 2011/0166222 A1 | 7/2011 | Kaplan | |
| 2011/0244043 A1 | 10/2011 | Xu et al. | |
| 2011/0276133 A1 | 11/2011 | Liu et al. | |
| 2011/0293687 A1 | 12/2011 | Bennett et al. | |
| 2012/0024300 A1 | 2/2012 | Dominguez et al. | |
| 2012/0046586 A1 | 2/2012 | Gurtner et al. | |
| 2012/0058076 A1 | 3/2012 | Widgerow | |
| 2012/0058167 A1 | 3/2012 | Widgerow | |
| 2012/0121534 A1 | 5/2012 | Thorel et al. | |
| 2012/0134951 A1 | 5/2012 | Stasko et al. | |
| 2012/0136323 A1 | 5/2012 | Stasko et al. | |
| 2012/0158054 A1 | 6/2012 | Stupak | |
| 2012/0172777 A1 | 7/2012 | Etchells | |
| 2012/0201915 A1 | 8/2012 | Stone | |
| 2012/0237627 A1 | 9/2012 | Debetencourt | |
| 2012/0238937 A1 | 9/2012 | Dean | |
| 2012/0251600 A1 | 10/2012 | Yu et al. | |
| 2012/0282300 A1 | 11/2012 | Masters et al. | |
| 2013/0011342 A1 | 1/2013 | Tamarkin et al. | |
| 2013/0028850 A1 | 1/2013 | Tamarkin et al. | |
| 2013/0121981 A1 | 5/2013 | Kaplan | |
| 2013/0131162 A1 | 5/2013 | Kaplan | |
| 2013/0131163 A1 | 5/2013 | Kaplan | |
| 2014/0314695 A1 | 10/2014 | Guilbaud | |

* cited by examiner

POLYSILICONE BASE FOR SCAR TREATMENT

CROSS-REFERENCE TO RELATED APPLICATIONS

The present application is a continuation of U.S. patent application Ser. No. 14/564,369, filed or Dec. 9, 2014, now U.S. Pat. No. 9,226,890, which claims priority to U.S. Provisional Patent Application No. 61/914,168, filed on Dec. 10, 2013, and U.S. Provisional Patent Application No. 62/028,915, filed on Jul. 25, 2014, the disclosures of all of the aforesaid patent applications being incorporated by reference herein.

FIELD OF INVENTION

The present invention relates to the fields of cosmetic or medical preparations, more specifically to preparations including a polysilicone base for the treatment and inhibition of scar tissue and stretch marks, or as a wound dressing.

BACKGROUND OF INVENTION

Polysilicone compositions have a variety of uses in the skin care industry, for example, as an emollient (also referred to as a "moisturizer"), as a skin protectant, as a cosmetic base, and as a vehicle for bioactive compounds. Polysilicone compositions are also useful in reducing the extent and appearance of scar tissue remaining after surgery or injury to the skin, or from skin conditions such as acne. They can also be used to reduce the appearance of uneven skin textures such as fine lines or acne.

An undesirable property of polysilicone compositions is that they can separate into phases, especially when cosmetic or bioactive compounds are added. This phase separation seriously reduces the usefulness of the composition, particularly as a cosmetic base or vehicle for other compounds.

SUMMARY OF INVENTION

In an embodiment of the present invention, a polysilicone base for application to the skin comprises a blend of polysilicones having different chemical structures and physical properties. In some embodiments, additional substances may be included in the polysilicone base to provide the polysilicone base with desirable rheological properties. In some embodiments, additional substances (e.g., emollients, skin conditioning agents, emulsifying agents, humectants, anti-oxidants, sunscreens, and antibiotic agents or other drugs) may be included in the polysilicone base to provide the polysilicone base with desirable medical, cosmetic, or aesthetic properties. In some embodiments, the polysilicone base is phase stable (i.e., it does not separate into phases).

In some embodiments, the polysilicone base, without further additives, may be applied to injured skin to minimize the appearance of scar tissue. In some embodiments, the polysilicone base may be applied to scar tissue to soften and reduce the scar tissue. In some embodiments, additional substances may be included in the polysilicone base to promote wound healing.

Embodiments of the present invention also include methods of making the polysilicone base of the present invention, and methods of using the polysilicone base of the present invention.

BRIEF DESCRIPTION OF FIGURES

Figures are not provided with the present disclosure, which is directed to a composition of matter and methods of making and using same.

DETAILED DESCRIPTION OF THE INVENTION

An embodiment of the present invention comprises a blend polysilicones, including medical grade polysilicones, selected to be applied to the skin in a spreadable form (e.g., as an ointment). The polysilicones may also be selected to provide the polysilicone base with desirable aesthetic properties (e.g., "look and feel"). It is desirable that the polysilicone base spread easily (spreadability), yet remain at the location at which it is applied, rather than running off of the application site. It is also desirable that the polysilicone base not irritate the skin, but provide the skin with a pleasant feel after it is applied (e.g., a smooth, silky, and non-greasy after-feel). The polysilicone base should also be stable, in that the components will not separate into phases. Other polysilicones which are not necessarily medical-grade, or other non-medical grade substances, may be included in the polysilicone base with the medical-grade polysilicones to provide the polysilicone base with the aforesaid properties.

In some embodiments, the polysilicones for the polysilicone base are selected to minimize the formation of scar tissue on skin damaged by such causes as cuts, burns, acne, or surgical wounds, and/or to soften and reduce scar tissue that has already formed. In some embodiments, substances with wound-healing properties may be added to the polysilicone base.

A polysilicone base according to an embodiment of the present invention includes: a blend of dimethicones of various viscosities and molecular weights; a volatile cyclosiloxane; a silicone elastomer; and a nanoparticulate mineral. Table 1 presents the composition of a polysilicone base according to an embodiment of the present invention, with the amounts of the various components shown as ranges.

TABLE 1

| Compound | % by Weight |
| --- | --- |
| Stearoxymethicone/dimethicone copolymer | 23.00-35.00 |
| Cyclopentasiloxane | 32.00-49.00 |
| Dimethicone (100 cSt) | 17.00-26.00 |
| Dimethicone (1,000 cSt) | 2.00-5.00 |
| Dimethicone (60,000 cSt) | 1.00-5.00 |
| Fumed silica | 0.40-0.80 |

Dimethicones are used in the polysilicone base as an active skin protectant and moisturizer. The physical properties of the dimethicones vary with viscosity and molecular weight, and may be used to impart a range of characteristics to the polysilicone base. At lower viscosities (e.g., 100 cSt), the dimethicones impart spreadability to the polysilicone base and dissolve high viscosity polysilicones that may otherwise not flow or be spreadable. At higher viscosities (e.g., 1,000 cSt), the dimethicones improve the feel of the polysilicone base, and provide a water-repellant protective barrier, while allowing the skin to perspire. At yet higher viscosities (e.g., 60,000 cSt), the dimethicones tend to provide a tacky feel to the polysilicone base, and are diluted to maintain the spreadability of the polysilicone base. Embodiments of the present invention may include other polysilicones in place of the dimethicones discussed above to produce a polysilicone base that has the properties of the exemplary polysilicone bases discussed elsewhere herein.

Cyclopentasiloxane is a volatile cyclic polysilicone that improves the spreadability of the polysilicone base, and provides the skin with a smooth, silky feel after the polysilicone base is applied thereto. In embodiments of the present invention, other volatile polysilicones may be used along with or in place of cyclopentasiloxane to improve the spreadability of the polysilicone base.

Stearoxymethicone/dimethicone co-polymer is a polysilicone elastomer, which tends to prevent phase separation of the various components of the polysilicone base. It also provides sebum absorption and oil control, and a soft-cushioning, powdery after-feel to the polysilicone base. In embodiments of the present invention, other polysilicone materials may be used along with or in place of stearoxymethicone/dimethicone co-polymer to prevent phase separation of the various components of the polysilicone base.

Fumed silica is included in the polysilicone base of Table 1 to further improve the rheology and thixotropy of the polysilicone base. Fumed silica tends to be composed of silica particles with high specific surface areas and sizes in the nanometer range. In embodiments of the present invention, other rheologic or thixotropic agents may be used along with or in place of fumed silica to form a polysilicone base having similar rheological or thixotropic properties to the exemplary polysilicone bases discussed herein.

The polysilicone base of the present invention may comprise other dimethicones, volatile cyclosiloxanes, polysilicone elastomers, and nanoparticulate minerals than those listed above. Surfactants, such as lauryl alcohol ethoxylates may be added to the polysilicone base in small amounts as emulsifiers to aid the elastomers in preventing separation of the components. In some embodiments, additional substances may be included in the polysilicone base to promote wound healing, or to add color or scent to the polysilicone base. When such additional substances are included in the polysilicone base, the amounts of the polysilicone compounds may be adjusted, or small amounts of other polysilicones added, to maintain the stability and rheological properties of the polysilicone base.

An exemplary embodiment of the polysilicone base of the present invention has the composition shown in Table 2.

TABLE 2

| Compound | Exemplary Trade Name | % by Weight |
| --- | --- | --- |
| Stearoxymethicone/dimethicone copolymer (98-99%)/Laureth-12 (1-2%) | Gransil EP-BD (Grant Industries) | 29.00 |
| Cyclopentasiloxane | ST Cyclomethicone 5-NF (Dow Corning) | 40.80 |
| Dimethicone (100 cSt) | Q7-9120 Silicone Fluid 100 CS #771324 (Dow Corning) | 22.00 |
| Dimethicone (1,000 cSt) | Q7-9120 Silicone Fluid 1,000 CS #791955 (Dow Corning) | 4.50 |
| Dimethicone (60,000 cSt) | KF96H 60,000 CS (DM-FLUID 60,000 CS) (Shin-Etsu) | 3.00 |
| Fumed silica (specific surface area of 175-225 m$^2$/g) | Aerosil 200 (Evonik) | 0.70 |
| TOTAL | | 100.00 |

The exemplary polysilicone base has a viscosity in the range of 2,200,000 to 3,200,000 cSt after 24 hours and spreads easily over the skin, yet remains at the location at which it is applied, rather than running off of the application site. The exemplary polysilicone base is expected to be non-irritating in normal use. The exemplary polysilicone base is phase stable.

In the exemplary polysilicone base, and in other embodiments of the present invention, one or more of the component polysilicones are recognized in the medical arts as being medical grade materials. In an embodiment of the present invention, the dimethicones having lower viscosities (e.g., 100 cSt and 1,000 cSt) and the cyclopentasiloxane are selected from among available medical grade materials. In the exemplary polysilicone base, and in other embodiments of the present invention, about 40% of the polysilicones are volatile polysilicones.

In a method of making a polysilicone base having a composition such as that of Table 1, the dimethicones, volatile cyclosiloxane, and silicone elastomer may be blended together in a sanitized vessel under anhydrous conditions, then homogenized. After further blending, the nanoparticulate mineral may be added, with concurrent mixing, and the resulting mixture homogenized. Additional blending may be needed to bring the mixture to the desired initial viscosity. Suitable blending rates and equipment, as well as blending times and temperatures, may be readily ascertained by those having ordinary skill in the art and possession of the present disclosure.

In a method of making the polysilicone base of Table 2, the desired amounts of the listed dimethicones, volatile cyclosiloxane, and silicone elastomer are added to a cleaned and sanitized vessel, blended, then homogenized. The fumed silica may then be added, with mixing, and the mixture may then be homogenized. A sample of the homogenized mixture may be tested for its initial viscosity. It the initial viscosity is out of specification (e.g., 1,700,000 to 2,500,000 cSt), additional blending or homogenization may be performed. The blending steps described above are carried out under anhydrous conditions in a nominal temperature range that will minimize the release of the volatile components. Suitable blending rates and equipment, as well as blending times and temperatures, may be readily ascertained by those having ordinary skill in the art and possession of the present disclosure. Additional components (e.g., substances to modify the aesthetic properties of the polysilicone base, or bioactive substances) may be mixed into the base.

Embodiments of the present invention may be used to inhibit the formation or reduce the appearance of scar tissue, which normally forms during the natural healing of wounds or other injuries. The scar tissue is formed from collagenous connective tissue that grows into the site of the wound. Hypertrophic scars form as raised areas or lumps above the wounded area of the skin. Such scars are formed by the formation of too much collagen relative to normal skin during the healing process. Keloid scars grow beyond the site of the wound, resulting in reddish tumor-like growths. Such a scar consists primarily of collagen. The growths are benign (i.e., not cancerous), but often have an unpleasant appearance or cause an itchy or burning sensation. Keloid scars may form during wound healing, but may also form spontaneously, with no known cause. Embodiments of the scar treatment base of the present invention, with or without therapeutic additives, may be applied over wounds to inhibit scar formation, or applied to scars that have already formed to reduce their appearance.

In a first method of using the polysilicone base of the present invention, the user applies a thick layer of the polysilicone base to the injured skin. The polysilicone base remains in place during the healing process, or until it is removed. In a second method of the using the polysilicone base of the present invention, the polysilicone base is applied to scar tissue and gently massaged to aid in softening and flattening the scar tissue.

It will be understood by those having ordinary skill in the art and possession of the present disclosure that the embodiments described herein are merely exemplary in nature and that a person skilled in the art may make many variations and modifications thereto without departing from the scope of the present invention. All such variations and modifications, are intended to be included within the scope of the invention as described in the attached claim(s).

We claim:

1. A polysilicone base for medical and cosmetic compositions, comprising:
   a first dimethicone fluid having a viscosity of about 100 cSt;
   a second dimethicone fluid having a viscosity of about 1,000 cSt;
   a third dimethicone fluid having a viscosity of about 60,000 cSt;
   volatile cyclopentasiloxane fluid;
   a stearoxymethicone/dimethicone copolymer; and
   a nanoparticulate silica, wherein said polysilicone base is phase stable.

2. The polysilicone base of claim 1, wherein said stearoxymethicone/dimethicone copolymer is present in said polysilicone base in an amount in the range of from about 23% to about 35% by weight.

3. The polysilicone base of claim 1, wherein said nanoparticulate silica is present in said polysilicone base in an amount in the range of from about 0.4% to about 0.8% by weight.

4. The polysilicone base of claim 1, wherein said polysilicone base has a viscosity in the range of 2,200,000 cSt to 3,200,000 cSt.

5. The polysilicone base of claim 1, wherein said polysilicone base spreads easily over the skin.

6. The polysilicone base of claim 1, wherein at least said first and second dimethicones and said volatile cyclopentasiloxane are of types recognized in the medical arts as medical grade materials.

7. The polysilicone base of claim 1, further comprising at leas one therapeutic agent for reducing the formation and/or appearance of scar tissue at a site of a wound.

* * * * *